(12) United States Patent
Naik

(10) Patent No.: US 6,910,371 B2
(45) Date of Patent: Jun. 28, 2005

(54) EXTENDED DURABILITY SENSING SYSTEM

(75) Inventor: Sanjeev Manubhai Naik, Troy, MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 10/079,962

(22) Filed: Feb. 21, 2002

(65) Prior Publication Data

US 2003/0154776 A1 Aug. 21, 2003

(51) Int. Cl.⁷ .................................................. G01M 19/00
(52) U.S. Cl. ...................................................... 73/118.1
(58) Field of Search ................................ 73/118.1, 31.06, 73/23.32, 25.01, 23.24, 117.3; 60/276, 274, 285, 284, 277; 204/412, 426; 205/787; 440/89 R; 340/506; 701/99, 76, 103; 123/520, 694, 492

(56) References Cited

U.S. PATENT DOCUMENTS

| | | | | |
|---|---|---|---|---|
| 4,007,589 A | * | 2/1977 | Neidhard et al. ............. 60/276 |
| 4,300,990 A | * | 11/1981 | Maurer .................... 204/195 S |
| 4,317,364 A | * | 3/1982 | Asano et al. ............... 73/117.3 |
| 4,467,602 A | * | 8/1984 | Izuka et al. ................. 60/276 |
| 5,056,308 A | * | 10/1991 | Kume et al. .................. 60/276 |
| 5,092,123 A | * | 3/1992 | Nada et al. ................... 60/274 |
| 5,331,808 A | * | 7/1994 | Koike .......................... 60/276 |
| 5,583,282 A | * | 12/1996 | Tom .......................... 73/31.03 |
| 5,807,306 A | * | 9/1998 | Shapland et al. ............. 604/21 |
| 5,985,118 A | * | 11/1999 | Makino et al. ............. 204/426 |
| 6,163,723 A | * | 12/2000 | Roberts et al. .............. 607/18 |
| 6,342,151 B1 | * | 1/2002 | Brosda et al. ........... 205/784.5 |
| 6,381,953 B1 | * | 5/2002 | Glugla et al. ................ 60/284 |
| 6,463,735 B2 | * | 10/2002 | Morinaga et al. ............ 60/277 |
| 6,477,830 B2 | * | 11/2002 | Takakura et al. ............. 60/277 |
| 6,589,409 B2 | * | 7/2003 | Miyashita et al. .......... 204/425 |
| 6,672,919 B1 | * | 1/2004 | Beson ..................... 440/89 R |

* cited by examiner

*Primary Examiner*—Eric S. McCall
*Assistant Examiner*—Octavia Davis
(74) *Attorney, Agent, or Firm*—Kathryn A. Marra

(57) ABSTRACT

The present invention provides a sensing system for monitoring an environment that includes at least two sensors and a control unit in communication with the sensors. At least one of the sensors is active providing an output signal to the control unit indicative of a sensed property, while the other sensor(s) is inactive and protected from the environment. During operation of the sensing system, if it is determined that the performance of the active sensor is abnormal, the inactive sensor is activated. Subsequently, the output signal of the abnormal sensor is ignored and the control unit utilizes an output signal of the previously inactive, but now active, sensor.

28 Claims, 5 Drawing Sheets

EXTENDED DURABILITY SENSING SYSTEM

BACKGROUND OF THE INVENTION

1. Field of the Invention

The present invention relates generally to sensing systems and more particularly to an extended durability sensing system employing one or more sequentially operated sensors.

2. Description of the Related Art

Sensing systems that employ one or more redundant sensors are well known in the art. The motivating factors for employing multiple sensors in these systems are typically to achieve fault tolerance through redundancy, improved measurement accuracy and the ability to cover a wider range of measurements in a finite period of time or space.

It is common to employ sensing systems in extreme temperature and/or corrosive environments, such as the exhaust-gas stream of an internal combustion engine, to monitor critical properties of the environment. The sensors in these systems, which are directly subjected to the monitored environment, may become damaged or otherwise wear-out over time resulting in, inter alia, a degradation in the performance of the sensors. Various approaches have been proposed to combat the premature performance degradation of these sensors. One such approach is to employ multiple redundant sensors that simultaneously monitor an environment. A limitation of this approach is that the performance of all the sensors usually degrades at approximately the same rate, which generally does not extend the durability of the sensing system. Another approach is to substitute conventional sensors with their high performance equivalent. A limitation of this approach is that these sensors typically cost substantially more than conventional sensors rendering them, in some installations, cost prohibitive to use.

SUMMARY OF THE INVENTION

The present invention overcomes the limitations of the prior art by providing an extended durability sensing system suitable for use in extreme temperature and/or corrosive environments. In an embodiment of the present invention, a sensing system is provided that includes at least two sensors and a control unit in communication with the sensors. One of the sensors is active providing an output signal to the control unit indicative of a sensed property of the monitored environment. The other sensor is inactive having at least a portion of the sensor that is protected from the monitored environment.

In one embodiment of the present invention, the inactive sensor includes a protective sheath that provides a physical barrier between the sensor and the monitored environment. During operation of the sensing system, if it is determined that the performance of the active sensor is abnormal, the inactive sensor is activated by removing the protective sheath. Subsequently, the output signal of the abnormal sensor is ignored and the control unit utilizes an output signal of the previously inactive, but now active, sensor.

In an alternate embodiment of the present invention, the inactive sensor is actuated from an inactive position, removed from the monitored environment, to an active position at least partially within the monitored environment. During operation of the sensing system, if it is determined that the performance of the active sensor is abnormal, the inactive sensor is activated by actuating the sensor into the monitored environment. Subsequently, the output signal of the abnormal sensor is ignored and the control unit utilizes an output signal of the previously inactive, but now active, sensor.

The sensing system of the present invention may be suitable for use in variety of environments, including those environments that tend to facilitate premature degradation in performance of conventional sensing devices. In particular, the sensing system of the present invention is suitable for use in monitoring the exhaust-gas stream of an internal combustion engine.

Among other advantages, the present invention provides an improved sensing system that maintains a specified level of performance over a longer period of time. The present invention advantageously employs at least one inactive sensor that is protected from the monitored environment and is activated upon determining that a currently active sensor is abnormal. Another advantage of the present invention is that it can employ multiple inactive sensors that may be sequentially activated over time to effectively extend the durability of the sensing system.

Various additional aspects and advantages of this invention will become apparent to those skilled in the art from the following detailed description of the preferred embodiment, when read in light of the accompanying drawings.

DESCRIPTION OF THE PREFERRED EMBODIMENT

Figure 1:
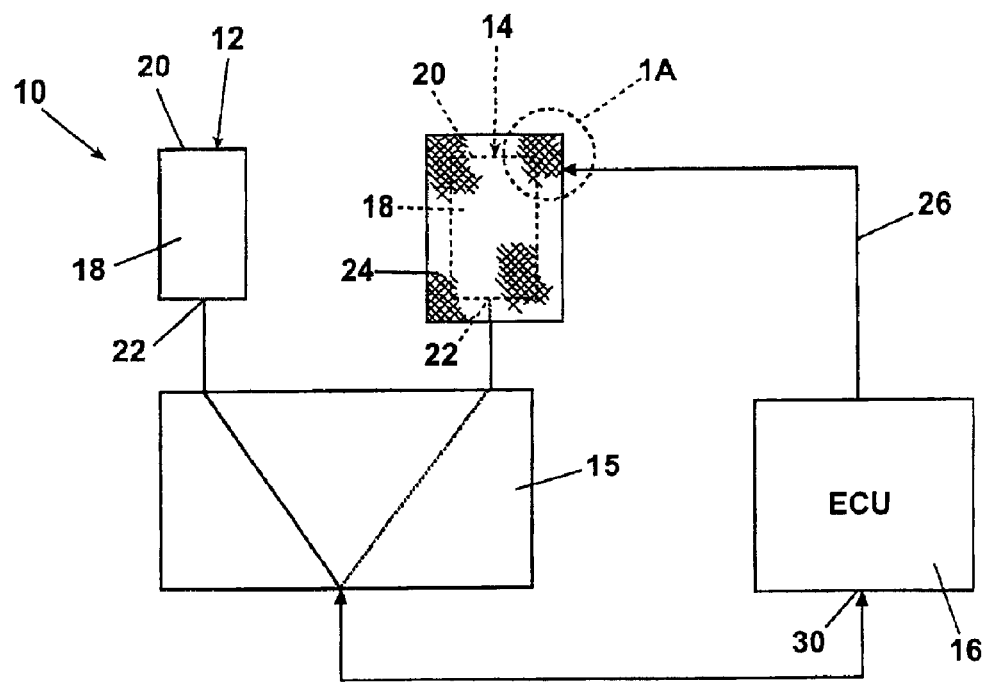
FIG. 1 is a schematic illustration of a sensing system according to an embodiment of the present invention.

Referring now to the drawings, preferred embodiments of the present invention are described in detail. Referring to FIG. 1, a schematic illustration of an embodiment of the present invention is shown in detail. A sensing system 10 is shown comprising at least one active sensor 12, at least one inactive sensor 14, a switching or multiplexing device 15 and an electronic control unit (ECU) 16 for sending and receiving signals to and from sensors 12, 14.

As illustrated in FIG. 1, each sensor 12, 14 generally includes a sensor body 18 having a portion 20 for sensing one or more properties of a monitored environment and at least one output 22 for transmitting an output signal indicative of the state of the sensed property. Sensors 12, 14 may be of the wide-range or switching-type and preferably include features or materials, such as stainless steel, that enable sensors 12, 14 to function in relatively harsh environments, such as the exhaust-gas stream of an internal combustion engine. However, it will be appreciated by those skilled in the art that the type of sensor is not limited to that shown and described above and that other sensors or sensor configurations are within the scope of this invention.

Figure 1A:
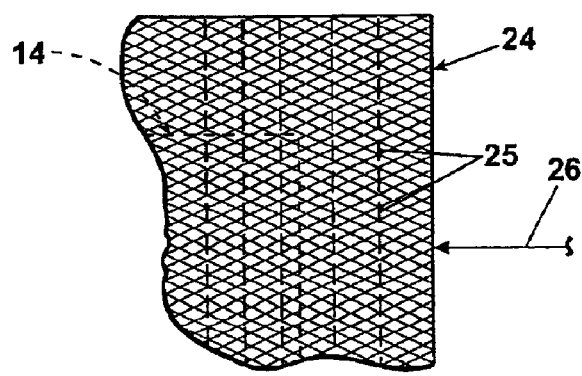
FIG. 1A is a partial detailed view of an inactive sensor prior to activation.

In one embodiment of the present invention, inactive sensor 14 includes a protective sheath 24 covering at least a portion of the sensor 14 exposed to the monitored environment and, more preferably, substantially all of body 18. As illustrated in FIG. 1A, protective sheath 24 preferably comprises a ceramic matrix that is held together by a plurality of fusible fibers 25 that are oriented to reinforce the ceramic matrix. Fibers 25 can be arranged in the ceramic matrix in any orientation, such as the liner orientation illustrated in FIG. 1A or a randomly positioned throughout the ceramic matrix. However, the number and orientation of fibers 25 will depend on various factors, such as the size of sensor 14, the composition of the ceramic matrix and the type of fusible fiber 25 used.

Fibers 25 are preferably formed of an electrically fusible metal having properties that allow them to easily melt or otherwise liquefy when subjected to an electrical current. However, fibers 25 may comprise other fusible materials, such as, for example, a polymer or metal alloy. Similarly, while the use of a ceramic is preferred due to its ability to withstand relatively high-temperatures and/or corrosive environments, it will be appreciated by those skilled in the art that sheath 24 may include other materials, such as, for example, thermoplastics. Sheath 24 is molded or otherwise formed around sensor 14 prior to connecting sensor 14 to sensing system 10.

The inactive sensor, more particularly sheath 24, is in communication with a source of electric current, such as the ECU 16. In order to activate the inactive sensor 14, the protective sheath 24 is removed by applying an electrical current to the metal fibers 25. In the presence of an appropriate electrical current, fibers 25 melt or otherwise liquefy, removing the structure need to hold sheath 24 together. Thus, the ceramic matrix dissolves or otherwise breaks-down leaving inactive sensor 14 exposed to the monitored environment. The electrical current needed to activate inactive sensor 14, denoted in FIGS. 1 and 1A as 26, is supplied by ECU 16 or other source of electrical current upon a determination that active sensor 12 is abnormal, as will be described in further detail below.

Figure 2:
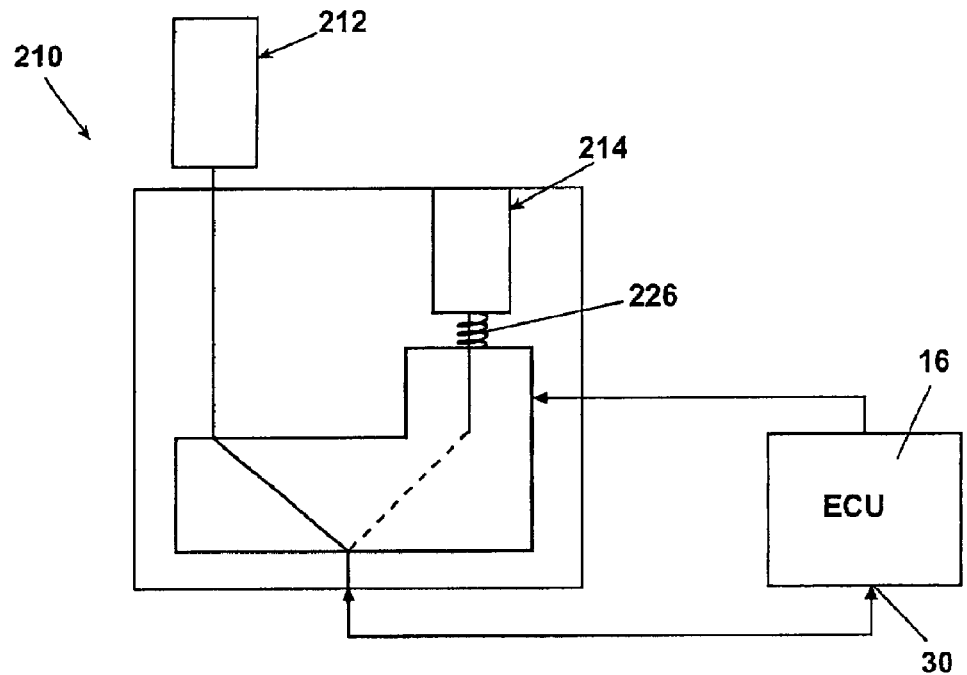
FIG. 2 is a schematic illustration of a sensing system according to an alternate embodiment of the present invention prior to activation of an inactive sensor.
Figure 3:
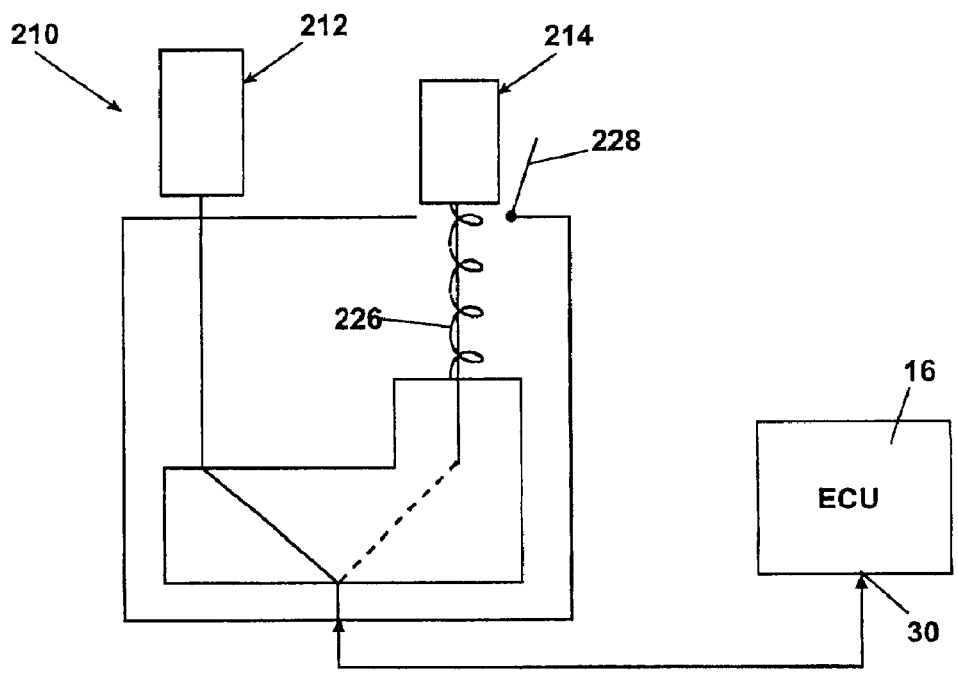
FIG. 3 is a schematic illustration of the sensing system of FIG. 2 after activation of the inactive sensor.

Referring to FIGS. 2–3, a schematic illustration of an alternate embodiment of the present invention is shown in detail. In this embodiment, a sensing system 210 is provided that includes an active sensor 212 that is actively monitoring an environment and an inactive sensor 214 at least partially removed or otherwise protected from the monitored environment. Upon determination that active sensor 212 is abnormal, inactive sensor 214 may be actuated from an inactive position, shown in FIG. 2, to an active position, shown in FIG. 3.

Figure 4A:
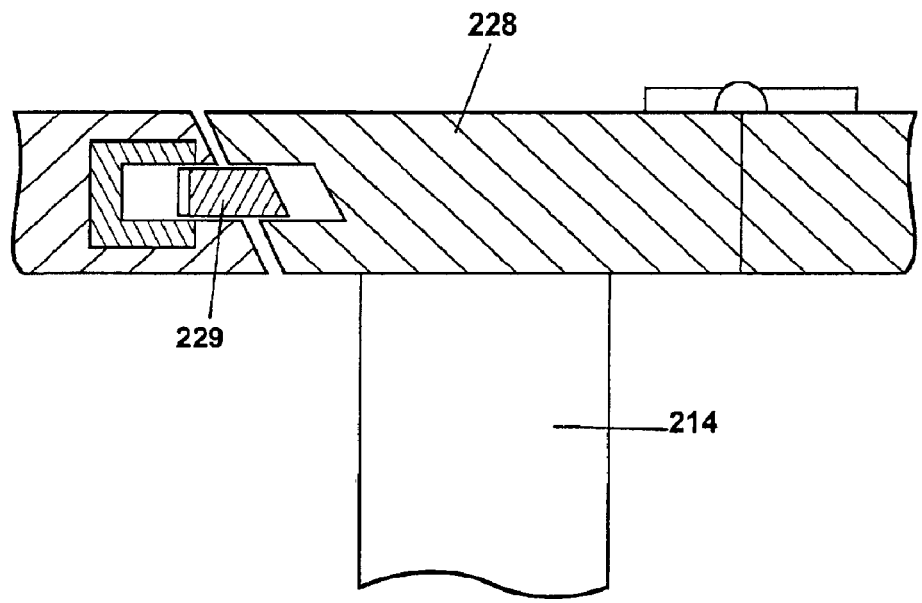
FIG. 4A is a partial cross sectional view showing the inactive sensor of FIG. 2 in the stored position.

In the inactive position, a resilient member 226, such as a compression spring, is compressed under inactive sensor 214 permitting inactive sensor 214 to be shielded from the monitored environment. A moveable gate 228, such as the hinged door illustrated in FIG. 4A, is disposed between inactive sensor 214 and the monitored environment. Gate 228 may be locked in a "closed" position, shown in FIG. 4A, by a locking pin 229 or other device that may actuated from a "locked" position, shown in FIG. 4A to a released position, shown in FIG. 4B. Pin 229 is preferably electromagnetically actuated, as illustrated in FIG. 4A, but may be actuated pneumatically, hydraulically or the like. Gate 228 acts primarily as a barrier between the environment and inactive sensor 214 and provides a means of releasing the inactive sensor 214 into the environment.

Figure 4B:
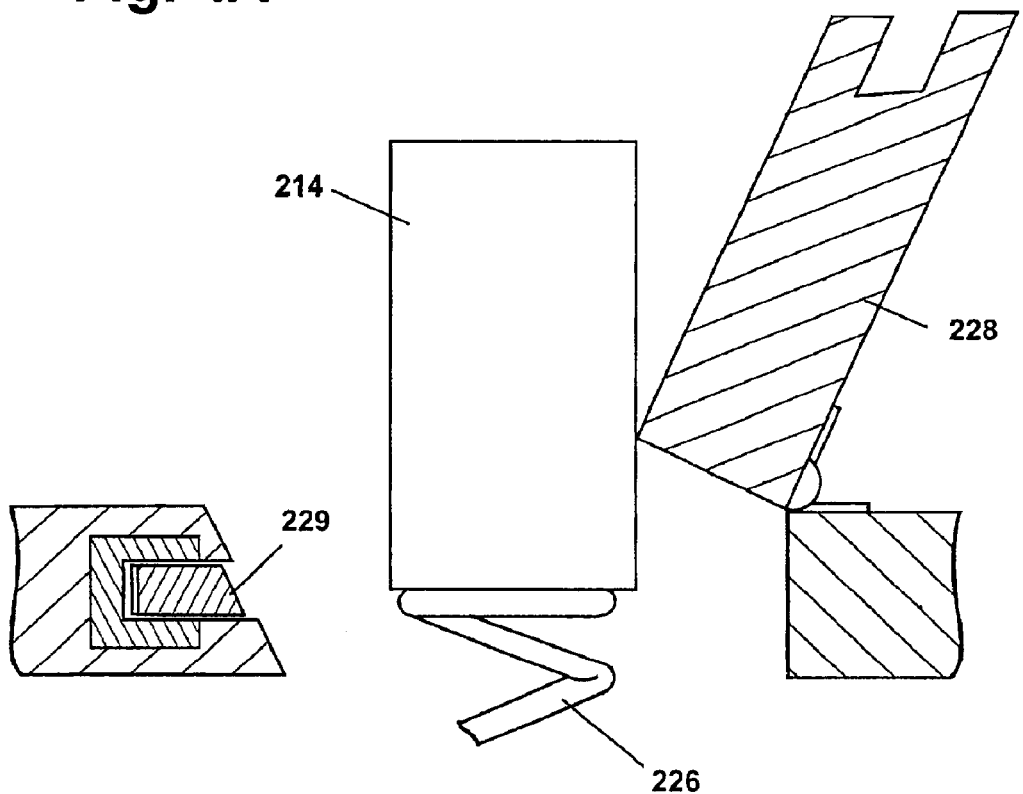
FIG. 4B is a partial cross sectional view showing the inactive sensor of FIG. 2 in the released position.

In order to activate inactive sensor 214, locking pin 229 is moved from the "locked" position, shown in FIG. 4A to the released position, shown in FIG. 4B. The actuated locking pin 229 allows the biasing force of resilient member 226 to overcome the forces holding inactive sensor 214 in the inactive position allowing inactive sensor 214 to be moved into the monitored environment. While this embodiment is described as employing a gate 228 as the means of protecting and retaining inactive sensor from the monitored environment, it is not intended to be so limited. Alternatively, other means of protecting inactive sensor 214 from the monitored environment may be employed, such as the protective sheath 24 described above. Additionally, other means of actuating inactive sensor 214 into the monitored environment may be employed, such as a pneumatically operated piston beneath sensor 214.

Referring to FIGS. 1 and 2, in each embodiment described above, ECU 16 includes at least one input 30 for processing output signals received from active sensor(s) 12, 212. ECU 16 is preferably microprocessor based having sufficient memory to store the logic rules, generally in the form of a computer program, needed to determine if active sensor 12, 212 is abnormal and for controlling activation of inactive sensor 14, 214. Abnormal performance of active sensor 12, 212 may be determined, for example, by comparing the output signal of active sensor 12, 212 to a theoretical range of acceptable output signal values or to one or more threshold values. If the output signal falls outside the theoretical range of acceptable values or exceeds one or more of the threshold values, active sensor 12, 212 may be deemed abnormal warranting activation of inactive sensor 14, 214. Alternatively, other criteria for determining abnormal performance of active sensor 12, 212 may be employed, such as, for example, automatically assuming that active sensor 12, 212 is abnormal after a predetermined period of time.

It will be appreciated by those skilled in the art that the present invention is not limited to any particular type or configuration of ECU 16 or to any specific control logic. What is essential to the present invention is that at least one sensor 12, 212 is actively monitoring an environment and at least one sensor 14, 214 is inactively protected from the environment awaiting activation. Moreover, what is essential to the present invention is that sensors communicate with some sort of control unit capable of activating at least one inactive sensor 14, 214 when the active sensor(s) 12, 212 becomes abnormal, and that the control unit include some sort of control logic capable of determining when active sensor 12, 212 is abnormal.

For additional durability, a plurality of sensors (one or more being initially active and the remaining being inactive) may be sequentially activated over time. Accordingly, sensing system 10 may employ two or more inactive sensors 14, 214 that are activated sequentially upon determination that a currently active sensor 12, 212 is abnormal. For example, in a sensing system having one initially active sensor and two inactive sensors, a first inactive sensor may be activated upon determination that the initially active sensor is abnormal and the second inactive sensor may be activated upon a determination that the first inactive, but now active, sensor is abnormal.

Operation of sensing systems 10 and 210 will be described with reference to FIGS. 5–8. While operation of sensing system 10 and 210 will be described as being employed to monitor the exhaust-gas stream of an internal combustion engine, the illustrative environment is not intended to be so limited. It will be appreciated that sensing system 10, 210 may be employed in other environments or applications, especially where performance of the sensors are subject to degradation when exposed to the monitored environment.

Figure 5:
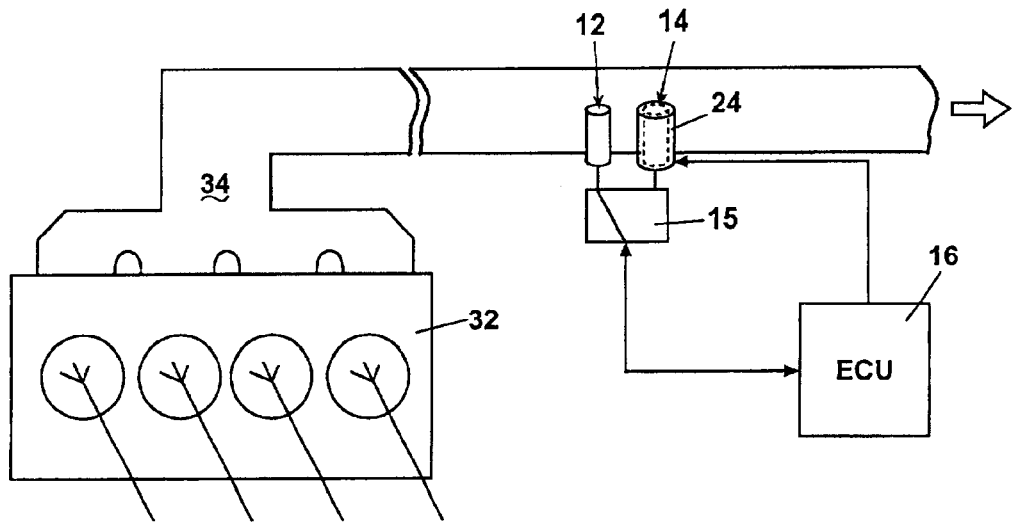
FIG. 5 is a schematic illustration showing the sensing system of FIG. 1 disposed in an exhaust-gas stream prior to activation of the inactive sensor.
Figure 6:
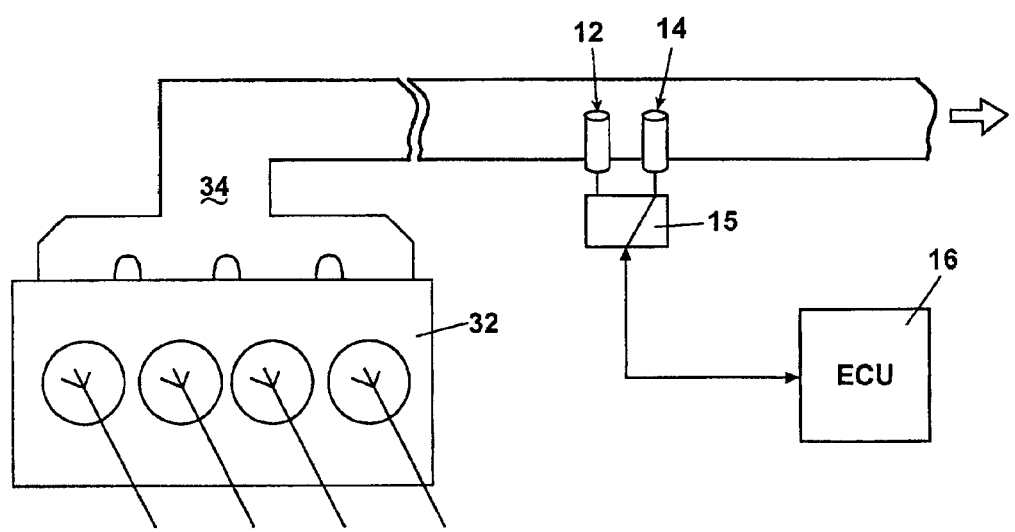
FIG. 6 is a schematic illustration showing the sensing system of FIG. 1 disposed in an exhaust-gas stream after activation of the inactive sensor.

FIGS. 5 and 6 are schematic illustrations showing sensing system 10 disposed in the exhaust-gas stream of an internal combustion engine. Reference number 32 denotes an internal combustion engine from which exhaust gas is discharged through one or more exhaust conduits 34, such as a manifold or tailpipe. At least one active sensor 12 is disposed at a point in exhaust conduit 34 downstream of engine 32. Additionally, at least one inactive sensor 14 is disposed proximate the active sensor 12, but is shielded from the exhaust stream by protective sheath 24.

Figure 7:
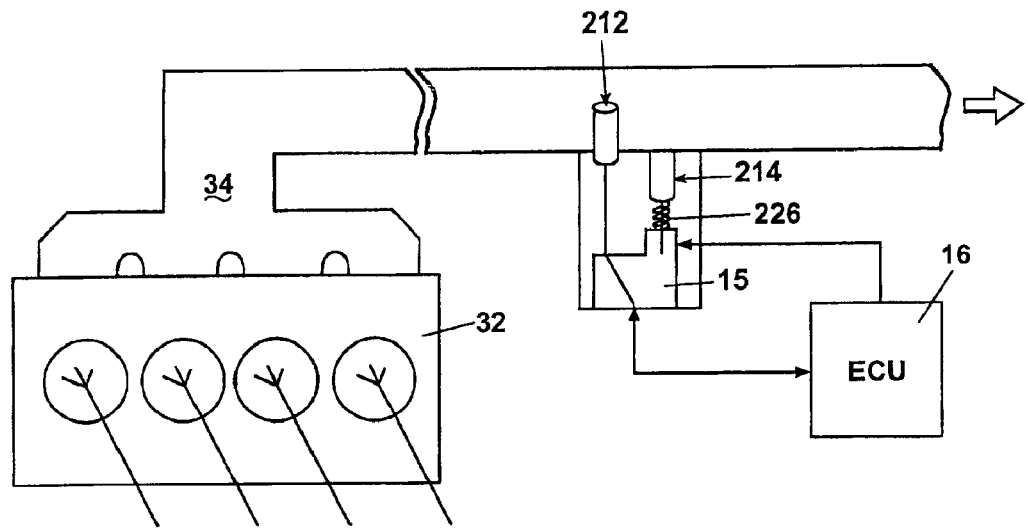
FIG. 7 is a schematic illustration showing the sensing system of FIG. 2 disposed in an exhaust-gas stream prior to activation of the inactive sensor.
Figure 8:
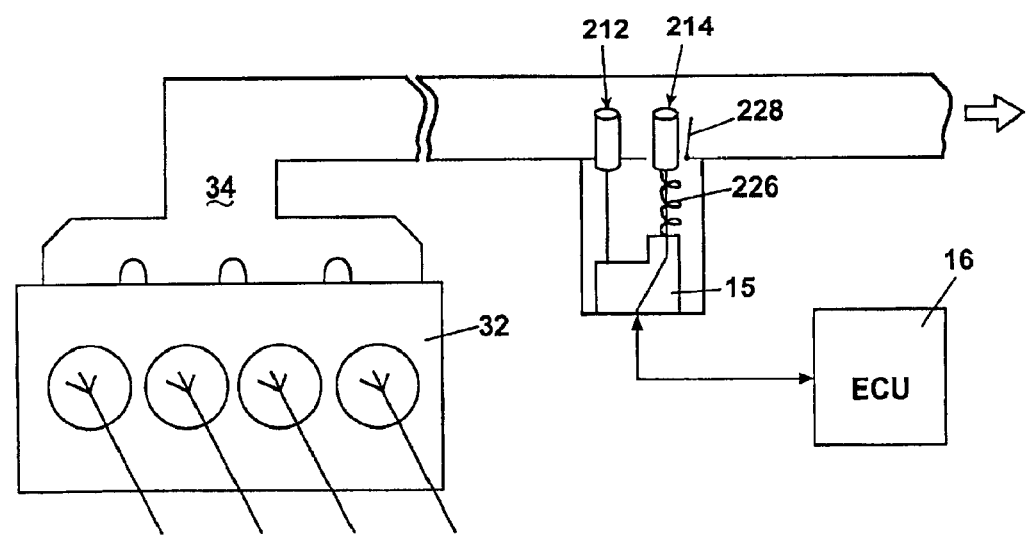
FIG. 8 is a schematic illustration showing the sensing system of FIG. 2 disposed in an exhaust-gas stream of an internal combustion engine after activation of the inactive sensor.

Similarly, FIGS. 7 and 8 are schematic illustrations showing the sensing system 210 disposed in an exhaust conduit 34 of internal combustion engine 32. At least one active sensor 212 is disposed at a point in exhaust conduit 34 downstream of the engine 32. Additionally, at least one inactive sensor 214 is disposed proximate the active sensor 212, but is shielded from the exhaust stream by gate 228, as shown in FIG. 4A.

Sensors 12, 212 and 14, 214 may comprise, for example, exhaust air-fuel ratio sensors, other exhaust-gas species concentration sensors, temperature sensors or pressure sensors. ECU 16 may comprise a typical vehicle powertrain control module (PCM) or other control unit that governs operation of various vehicle operating systems. Switching device 15 is preferably provided between the active and inactive sensors 12, 212 and 14, 214, respectively, permitting active sensor 12, 212 to communicate with ECU 16. When more than one active sensor 12, 212 or inactive sensor 14, 214 is used, a multiplexing device may be used in place of switching device 15 to place the multiple active sensors 12, 212 in simultaneous communication with ECU 16. As further illustrated in FIGS. 5 and 7, each inactive sensor 14, 214 or corresponding actuating means is in direct communication with ECU 16 such that an electrical signal may be provided by ECU 16 to activate each inactive sensor 14, 214.

Referring still to FIGS. 5 and 7, active sensor 12, 212 is initially exposed to the exhaust-gas stream that exits engine 32 and inactive sensor 14, 214 remains removed from the exhaust-gas stream awaiting activation. During operation of engine 32, active sensor 12, 212 produces an output signal to ECU 16 indicative of a measured property of the monitored exhaust-gas stream. The output signal is routed through switching device 15, or multiplexing device in the case of multiple sensors, into ECU 16.

At some point in time when the performance of active sensor 12, 212 is determined to be abnormal, an electrical signal is issued by ECU 16 to activate inactive sensor 14, 214. Referring to FIG. 6, in the case of inactive sensor 14, the electrical signal is in the form of an electrical current that removes protective sheath 24 from inactive sensor 14, as described above, resulting in sensor 14 being activated.

Alternatively, as illustrated in FIGS. 7 and 8, inactive sensor 214 is actuated from an inactive position, shown in FIG. 7, to an active position, shown in FIG. 8, resulting in inactive sensor 214 being activated.

Subsequent to the activation of inactive sensor 14, 214, switching device 15 (or multiplexing device in the case of multiple sensors) is automatically adjusted by ECU 16 such that an output signal produced by the previously inactive, but now active, sensor 14, 214 is routed to ECU 16. As a precaution, ECU 16 may be programmed to test the performance of sensor 14, 214 prior to deactivating or otherwise ignoring the output signal produced by active sensor 12, 212. If the output of sensor 14, 214 is deemed to be acceptable, the initially active sensor 12, 212 is ignored and the output signal from the previously inactive, but now active, sensor 14, 214 is utilized by ECU 16 to monitor the properties of the exhaust-gas stream.

Among other advantages, the present invention provides an improved sensing system that maintains a specified level of performance over a longer period of time. Unlike the prior art, the present invention advantageously employs at least one inactive sensor 14, 214 that is protected from the monitored environment and is activated upon determining that a currently active sensor 12, 212 is abnormal. Another advantage of the present invention is that it can employ multiple inactive sensors 14, 214 that may be sequentially activated over time to effectively extend the durability of the sensing system.

Although certain preferred embodiments of the present invention have been described, the invention is not limited to the illustrations described and shown herein, which are deemed to be merely illustrative of the best modes of carrying out the invention. A person of ordinary skill in the art will realize that certain modifications and variations will come within the teachings of this invention and that such variations and modifications are within its spirit and the scope as defined by the claims.

What is claimed is:

1. A sensing system for monitoring an environment comprising:
   at least two sensors, at least one of the sensors being active and at least one of the sensors being inactive, the active sensor being exposed to said monitored environment and the inactive sensor being unexposed to the monitored environment; and
   a control unit in communication with the sensors for activating at least one of the inactive sensors by exposing it to the environment when the active sensor is deemed abnormal.

2. The sensing system of claim 1, wherein at least a portion of the inactive sensor is covered by a protective sheath.

3. The sensing system of claim 2, wherein the protective sheath is a ceramic matrix having a fusible fiber reinforcement.

4. The sensing system of claim 2, wherein the inactive sensor is activated by removing the protective sheath.

5. The sensing system of claim 1, wherein the inactive sensor is activated by actuating the inactive sensor from an inactive position unexposed to the monitored environment to an active position exposed to the monitored environment.

6. The sensing system of claim 5, wherein the inactive sensor is actuated to the active position by a resilient biasing member.

7. The sensing system of claim 1, further including a switching device for switching between the use of the active sensor to one or more of the inactive sensors when the control unit has determined that the active sensor is abnormal.

8. The sensing system of claim 7, wherein the switching device has multiplexing capability.

9. The sensing system of claim 1, wherein the active sensor is deemed abnormal after a predetermined period of time.

10. The sensing system of claim 1, wherein the active sensor supplies an output signal to the control unit.

11. The sensing system of claim 10, wherein the active sensor is deemed abnormal when the output signal falls outside a predetermined range of acceptable output signals.

12. A sensing system for monitoring an exhaust-gas stream of an internal combustion engine, comprising:

at least two sensors disposed in the exhaust-gas stream, at least one of the sensors being active and exposed to the exhaust-gas stream and at least one of sensors being inactive and unexposed to the exhaust-gas stream; and a control unit in communication with the sensors for activating at least one of the inactive sensors by exposing it to the environment when the active sensor is deemed abnormal.

13. The sensing system of claim 12, wherein the sensors comprise at least one of an exhaust-gas species concentration sensor, an exhaust-gas temperature sensor and an exhaust-gas pressure sensor.

14. The sensing system of claim 12, wherein at least a portion of the inactive sensor is covered by a protective sheath.

15. The sensing system of claim 14, wherein the protective sheath is a ceramic matrix having a fusible fiber reinforcement.

16. The sensing system of claim 14, wherein the inactive sensor is activated by removing the protective sheath.

17. The sensing system of claim 12, wherein the inactive sensor is activated by actuating the inactive sensor from an inactive position unexposed to the monitored environment to an active position exposed to the monitored environment.

18. The sensing system of claim 17, wherein the inactive sensor is actuated to the active position by a resilient biasing member.

19. The sensing system of claim 12, further including a switching device for switching between the use of the active sensor to one or more of the inactive sensors when it is determined that the active sensor is abnormal.

20. The sensing system of claim 12, wherein the active sensor is deemed abnormal after a predetermined period of time.

21. The sensing system of claim 12, wherein the active sensor supplies an output signal to the control unit.

22. The sensing system of claim 21, wherein the active sensor is deemed abnormal when the output signal falls outside a predetermined range of acceptable output signals.

23. A method of maintaining the performance of a sensing system for monitoring an environment, comprising the steps of:

providing at least two sensors in the sensing system, at least one of the sensors being active and at least one of the sensors being inactive, the active sensor being exposed to and actively monitoring the environment and the inactive sensor being unexposed to and not actively monitoring the environment;

determining when at least one of the active sensors is abnormal; and exposing at least one of the inactive sensors to the monitored environment upon a determination that at least one of the active sensors is abnormal.

24. The sensing system of claim 23, wherein at least a portion of the inactive sensors is covered by a protective sheath.

25. The sensing system of claim 24, wherein the protective sheath is a ceramic matrix having a fusible fiber reinforcement.

26. The sensing system of claim 25, wherein the step of exposing at least one of the inactive sensors to the monitored environment comprises removing the protective sheath.

27. The sensing system of claim 23, wherein the step of exposing at least one of the inactive sensors to the monitored environment comprises actuating the inactive sensor from an inactive position unexposed to the monitored environment to an active position exposed to the monitored environment.

28. The method of claim 23, further including the step of switching between the use of at least one of the active sensors to at least one of the inactive sensors when it is determined that at least one of the active sensors is abnormal.

* * * * *